United States Patent [19]

Grosse-Bley et al.

[11] Patent Number: 6,063,394
[45] Date of Patent: May 16, 2000

[54] INJECTION FORMULATIONS OF AVERMECTINS AND MILBEMYCINS BASED ON CASTOR OIL

[75] Inventors: Michael Grosse-Bley; Richard Kujanek, both of Köln, Germany

[73] Assignee: Bayer Aktiengesellschaft, Leverkusen, Germany

[21] Appl. No.: 09/155,836

[22] PCT Filed: Mar. 27, 1997

[86] PCT No.: PCT/EP97/01569

§ 371 Date: Oct. 6, 1998

§ 102(e) Date: Oct. 6, 1998

[87] PCT Pub. No.: WO97/37653

PCT Pub. Date: Oct. 16, 1997

[30] Foreign Application Priority Data

Apr. 9, 1996 [DE] Germany ............ 196 13 972

[51] Int. Cl.[7] .................... A61F 13/00
[52] U.S. Cl. .................... 424/422; 514/943
[58] Field of Search .................... 424/422, 424; 514/943

[56] References Cited

U.S. PATENT DOCUMENTS

| 4,199,569 | 4/1980 | Chabala et al. ............ 424/180 |
| 4,310,519 | 1/1982 | Albers-Schonberg et al. ......... 424/181 |
| 4,916,120 | 4/1990 | Roben et al. ............ 514/30 |
| 5,510,117 | 4/1996 | Abate ............ 424/489 |

FOREIGN PATENT DOCUMENTS

| 0 045 655 | 3/1985 | European Pat. Off. . |
| 0 146 414 | 10/1989 | European Pat. Off. . |
| 0 393 890 | 8/1992 | European Pat. Off. . |
| 0 525 307 | 2/1993 | European Pat. Off. . |
| 0 535 734 | 7/1993 | European Pat. Off. . |
| 0 413 538 | 10/1993 | European Pat. Off. . |
| 1390336 | 6/1973 | United Kingdom . |

OTHER PUBLICATIONS

B. Kruss, Acta Pharm. Technol. 35 (4) (month unavailable) 1989, pp. 187–196.
I. Putter et al, Experentia 37 (month unavailable) 1981, p. 963.
Chem. Soc. Re. 1991, 20, (month unavailable) 1991, pp. 271–339.
G.T. Carter et al, J. Chem Soc., Chem Commun., (month unavailable) 1987, p. 402–404.
Vet. Parasitology, 49, Goudie et al, (month unavailable) 1993, pp. 5–15.

*Primary Examiner*—Thurman K. Page
*Assistant Examiner*—Todd D Ware
*Attorney, Agent, or Firm*—Joseph C. Gil; Godfried R. Akorli

[57] ABSTRACT

Injection formulations of avermectins and milbemycins based on castor oil are disclosed.

5 Claims, No Drawings

INJECTION FORMULATIONS OF AVERMECTINS AND MILBEMYCINS BASED ON CASTOR OIL

The invention relates to new injection formulations of avermectins and milbemycins in animals, based on castor oil.

Injection formulations of ivermectin are disclosed in EP-A 146 414. The formulations contain a solvent mixture of propylene glycol and glycerol formal in the ratio 60:40 v/v. It is known of propylene glycol that in certain concentrations it can cause local intolerabilities (see review: B. Kruss, Acta Pharm. Technol. 35(4) (1989) 187–196). The precipitation of the water-insoluble active compound ivermectin can also occur in the tissue around the administration site. Thus when using corresponding formulations marked swellings and tissue incompatibilities were observed at the injection sites, some of which only receded after several weeks.

Injection formulations of specific avermectins are disclosed in EP-A 393 890. They are oil formulations based on sesame oil and ethyl oleate in the ratio 90:10 v/v. These formulations are tolerable, but have the disadvantage that on storage in a refrigerator at 4° C. a flocculent precipitate is formed even after a few days.

Further injection formulations of avermectins are disclosed in EP-A 45 655. The formulations described there contain comparatively high amounts of emulsifiers and in some cases are not very tolerable.

Injection formulations of avermnectins which contain triacetin (glycerol triacetate) are described in EP-A 413 538. In EP-A 535 734, injection formulations of avermectins based on triacetin and hydrogenated castor oil are described.

Further formulations for the injection of milbemycins and avermectins are described in EP-A 525 307. The formulations are prepared by fusing glycerol tristearate with the active compound and mixing with an oily neutral triglyceride and emulsifying using, for example, methylcellulose and salts. The average particle size in the microemulsion thus obtained should be between 25 and 300 $\mu$m.

The present invention relates to injection formulations of avermectins and milbemycins based on castor oil.

The formulations preferably contain 1. active compound 0.1 to 10% by weight
2. castor oil 15 to 50% by weight
3. One or more co-solvents from the series consisting of vegetable or synthetic fatty acid esters of mono- or polyhydric alcohols, aliphatic or aromatic alcohols, cyclic carbonates in concentrations of 30 to 85% by weight
4. if appropriate, further auxiliaries.

The formulations according to the invention have an outstanding solubility for the active compounds.

The high viscosity of castor oil can be adjusted to a desired lower value by addition of medium-chain triglycerides or propylene glycol octanoate/decanoate or ethyl oleate. Additionally, the solubility of the active compound can be improved, the viscosity further reduced and the bioavailability of the active compound improved by addition of relatively small volumes of hydrophilic solvents such as benzyl alcohol, propylene glycol or propylene carbonate with retention of a single-phase system. The new formulations are extremely highly tolerable and have a high bioavailability.

The active compounds employed in the formulations according to the invention are known.

Avermectins were isolated from the microorganism Streptomyces avermitilis as microbial metabolites (U.S. Pat. No. 4,310,519) and can occur essentially as a mixture consisting of the eight components $A_{1a}$, $A_{1b}$, $A_{2a}$, $A_{2b}$, $B_{1a}$, $B_{1b}$, $B_{2a}$, and $B_{2b}$ (I. Putter et al., Experentia 37 (1981) p. 963, Birkhäuser Verlag (Switzerland)). In addition, the synthetic derivatives, in particular 22,23-dihydroavermectin $B_1$ (ivermectin), are also of interest (U.S. Pat. No. 4,199,569). Milbemycin B-41 D was isolated from Streptomyces hygroscopicus by fermentation (cf. "Milbemycin: Discovery and Development", I. Junya et al., Annu. Rep. Sankyo Res. Lab. 45 (1993), pp.1–98; JP Pat. 8,378,549; GB 1,390,336).

The use of the avermectins, e.g. 22,23-dihydroavermectins $B_1$, (ivermectin) and milbemycins as endoparasiticides is known and is the subject of numerous patent applications and review articles (e.g. biological actions in: "Ivermectin and Abamectin", W. C. Campbell, Ed., Springer Verlag, New York, N.Y., 1989; "Avermectins and Milbemycins Part II" H. G. Davies et al., Chem. Soc. Rev. 20 (1991) pp. 271–339; chemical modifications in: G. Lukacs et al. (Eds.), Springer Verlag, N.Y., (1990), Chapter 3; Cydectin® [moxidectin and derivatives]: G. T. Carter et al., J. Chem. Soc. Chem. Commun. (1987), pp. 402–404); EP 423 445-Al) "Doramectin —a potent novel endectocide" A. C. Goudie et al., Vet. Parasitol. 49 (1993), pp. 5–15).

Avermectins and their derivatives which may be particularly emphasized are those of the general formula (I)

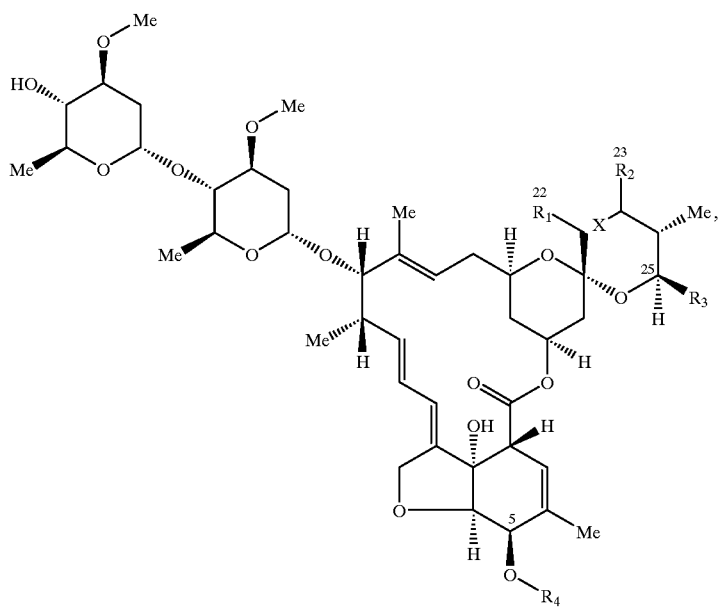

(I)

in which
the radicals $R^1$ to $R^4$ have the meaning indicated in Table 1 which follows and X can be a single or double bond between the $C_{22}$- and $C_{23}$- positions ($—C_{22}R^1—X—C_{23}R^2—$).

If there is a double bond, there are no substituents ($R_1$, $R^2$) in the $C_{22}$- and $C_{23}$-positions.

TABLE 1

| Macrocyclic lactone | $—C_{22}R^1—X—C_{23}R^2—$ | $R^3$ | $R^4$ |
| --- | --- | --- | --- |
| Avermectin $A_{1a}$ | —CH=CH— | -sec-Bu | —Me |
| Avermectin $A_{1b}$ | —CH=CH— | -iso-Pr | —Me |
| Avermectin $A_{2a}$ | —CH$_2$—CHOH— | -sec-Bu | —Me |
| Avermectin $A_{2b}$ | —CH$_2$—CHOH— | -iso-Pr | —Me |
| Avermectin $B_{1a}$ | —CH=CH— | -sec-Bu | —H |
| Avermectin $B_{1b}$ | —CH=CH— | -iso-Pr | —H |
| Avermectin $B_{2a}$ | —CH$_2$—CHOH— | -sec-Bu | —H |
| Avermectin $B_{2b}$ | —CH$_2$—CHOH— | -iso-Pr | —H |
| 22,23-dihydroavermectin $B_{1a}$ | —CH$_2$—CH$_2$— | -sec-Bu | —H |
| 22,23-dihydroavermectin $B_{1b}$ | —CH$_2$—CH$_2$— | -iso-Pr | —H |
| Doramectin | —CH=CH— | —Chx | —H |

22,23-Dihydroavermectin $B_1$, is ivermectin;

sec-Bu=secondary butyl; iso-Pr=isopropyl; Chx=cyclohexyl; -Me=methyl

As a rule, the avermectins and 22,23-dihydroavermectins $B_1$ (ivermectin) of the general formula (I) are employed as mixtures. Of particular interest in this connection is the product abamectin, which essentially contains the avermectins $B_1$, and their hydrogenation products, the 22,23-dihydroavermectins $B_1$ (ivermectin).

The compounds of the macrocyclic lactones marked with "b" which in the $C_{25}$-position have an iso-propyl radical, do not necessarily have to be separated from the "a" compounds, which have a sec-butyl group in the $C_{25}$-position. Generally the mixture of both substances, consisting of >80% sec-butyl derivative ($B_{1a}$) and <20% iso-propyl derivative ($B_{1b}$), is isolated, and can be used according to the invention. Additionally, in the stereoisomers the substituents in the $C_{13}$- and $C_{23}$-positions can be arranged on the ring system both in the α- and β-positions, i.e. are located above or below the plane of the molecule. In each case, all stereoisomers are taken into account according to the invention.

The milbemycins may be mentioned particularly. The milbemycins have the same macrolide ring structure as the avermectins or 22,23-dihydroavermectins $B_1$ (ivermectin), but carry no substituents (i.e. missing oleandrose disaccharide fragment) in position 13 ($R^5$=hydrogen).

As examples of milbemycins from the class of macrocyclic lactones, the compounds having the general formula (II) may be mentioned

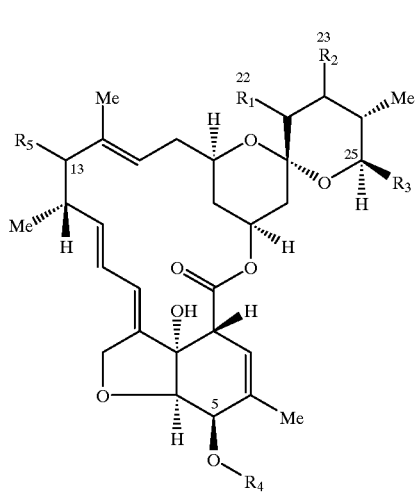

(II)

in which
the radicals $R^1$ to $R^4$ have the meaning indicated in Table 2 which follows:

TABLE 2

| Macrocyclic lactone | $R^1$ | $R^2$ | $R^3$ | $R^4$ | $R^5$ |
| --- | --- | --- | --- | --- | --- |
| Milbemycin B41 D | —H | —H | -iso-Pr | —H | —H |
| Nemadectin | —H | —OH | —CH=C(Me)—CH(Me)—Me | —H | —H |
| Moxidectin | —H | =N—O—Me | —CH=C(Me)—CH(Me)—Me | —H | —H | iso-Pr = isopropyl

The active compounds which may be very particularly emphasized are
avermectin $B_{1a}/B_{1b}$ (Abamectin),
22,23-dihydroavermectin $B_{1a}/B_{1b}$ (ivernectin),
doramectin,
moxidectin.

The active compounds are present in the formulations according to the invention in concentrations from 0.1 to 10% by weight, preferably from 0.5 to 5% by weight, particularly preferably 1–2% by weight.

The castor oil employed in the formulations according to the invention is known. It is used here in concentrations of 15 to 50% by weight.

The cosolvents employed in the formulations according to the invention are known.

Suitable vegetable or synthetic fatty acid esters of polyhydric alcohols (oils) are fatty acid triglycerides, preferably fatty acid triglycerides of medium chain length. Particularly suitable are neutral oils, such as neutral vegetable oils, and in particular fractionated coconut oils, such as are known and commercially available, for example, under the trade name Miglyol, reference again being made to Lexikon der Hilfsstoffe [Encyclopaedia of Auxiliaries], 3rd Edition, pages 808 to 809, (1989) by Fiedler. These include, for example: Miglyol 810: this is a fractionated coconut oil which contains triglycerides of caprylic acid and capric acid and has a molecular weight of approximately 520. It has a fatty acid composition with $C_6$ at most 2%, $C_8$ approximately 65 to 75%, $C_{10}$ approximately 25 to 35% and $C_{12}$ at most 2%, has an acid number of approximately 0.1, has a saponification number of approximately 340 to 360 and has an iodine number of at most 1. Miglyol 812: this is a fractionated coconut oil which contains triglycerides of caprylic acid and capric acid and has a molecular weight of approximately 520. It has a fatty acid composition with $C_6$ at most 3%, $C_8$ approximately 50 to 65%, $C_{10}$ approximately 30 to 45% and $C_{12}$ at most 5%, has an acid number of approximately 0.1, has a saponification number of approximately 330 to 345 and has an iodine number of at most 1. Miglyol 818: triglycerides of caprylic acid, capric acid and linolenic acid having a molecular weight of approximately 510. It has a fatty acid composition with $C_6$ at most 3%, $C_8$ approximately 45 to 60%, $C_{10}$ approximately 25 to 40%, $C_{12}$ approximately 2 to 5% and $C_{18}$ approximately 4 to 6, $C_6$ has an acid number of approximately 0.2, has a saponification number of approximately 315 to 335 and has an iodine number of at most 10. Captex 355[(1)]: triglyceride of caprylic acid and capric acid. This triglyceride has a fatty acid content of caproic acid of approximately 2%, of caprylic acid of approximately 55% and of capric acid of approximately 42%. It has an acid number of at most 0.1, has a saponification number of at most approximately 325 to 340 and has an iodine number of at most 0.5. Furthermore, also suitable are triglycerides of caprylic acid and capric acid, such as the products known and commercially available under the trade name Myritol, for which reference is made to Lexikon der Hilfsstoffe [Encyclopaedia of Auxiliaries], 3rd Edition, page 834 (1989) by Fiedler. The product Myritol 813 belonging to these has an acid number of at most 1, has a saponification number of approximately 340 to 350 and has an iodine number of approximately 0.5.

The following are additionally suitable: monoglycerides, diglycerides and mono/diglycerides, in particular esterification products of caprylic acid or capric acid with glycerol. Preferred products of this class are, for example, the products which contain monoglycerides and diglycerides of caprylic acid/capric acid or consist essentially or virtually thereof, and such products are commercially available under the trade name Imwitor, for which reference is made to Lexikon der Hilfsstoffe [Encyclopaedia of Auxiliaries], 3rd Edition, page 645 (1989) by Fiedler. A particularly suitable product from this class for use in the compositions according to the invention is the product Imwitor 742, which is an esterification product of a mixture of approximately 60 parts by weight (ppw) of caprylic acid and approximately 40 parts by weight (ppw) of capric acid with glycerol. Imwitor 742 is usually a yellowish crystalline mass, which is liquid at approximately 26° C. It has an acid number of at most 2, has an iodine number of at most 1, has a saponification number of approximately 235 to 275, contains approximately 40 to 50% of monoglycerides, has a content of free glycerol of at most 2%, has a melting point of approximately 24 to 26° C., contains unsaponifiable constituents of at most 0.3% and has a peroxide number of at most 1.

Sorbitan fatty acid esters of the most different types known, such as are commercially available, for example, under the trade name Span, and these include, for example, sorbitan monolauryl ester, sorbitan monopalmityl ester, sorbitan monostearyl ester, sorbitan tristearyl ester, sorbitan monooleyl ester and sorbitan trioleyl ester, and for these, reference is made, for example, to Lexikon der Hilfsstoffe [Encyclopaedia of Auxiliaries], 3rd Edition, pages 1139 to 1140 (1989) by Fiedler.

Pentaeryttritol fatty acid and polyalkylene glycol ethers, such as pentaerythritol dioleate, pentaerythritol distearate, pentaerythritol monolaurate, pentaerythritol polyglycol ether and pentaerythritol monostearate and also pentaerythritol fatty acid esters, for which reference is made to Lexikon der Hilfsstoffe [Encyclopaedia of Auxiliaries], 3rd Edition, pages 923 to 924 (1989) by Fiedler.

Monoglycerides, such as glycerol monooleate, glycerol monopalmitate and glycerol monostearate, such as are known and commercially available, for example, under the trade names Myvatex, Myvaplex and Myverol, for which reference is made to Lexikon der Hilfsstoffe [Encyclopaedia of Auxiliaries], 3rd Edition, page 836 (1989) by Fiedler, and acetylated, for example monoacetylated and diacetylated, monoglycerides, such as are known and commercially available, for example, under the trade name Myvacet, for which reference is made to Lexikon der Hilfsstoffe [Encyclopaedia of Auxiliaries], 3rd Edition, page 835 (1989) by Fiedler.

Mono- and difatty acid esters of propylene glycol, such as propylene glycol dicaprylate, propylene glycol dilaurate, propylene glycol hydroxystearate, propylene glycol isostearate, propylene glycol laurate, propylene glycol ricinoleate, propylene glycol stearate and the like, for which reference is made to Lexikon der Hilfsstoffe [Encyclopaedia of Auxiliaries], 3rd Edition, pages 1013 ff. (1989) by Fiedler. Particularly preferred is propylene glycol caprylic acid capric acid diester, which is known and commercially available under the trade name Miglyol 840, for which reference is made to Lexikon der Hilfsstoffe [Encyclopaedia of Auxiliaries], 3rd Edition, page 809 (1989) by Fiedler. Miglyol 840 has a fatty acid content of $C_6$ of at most approximately 3 per cent, $C_8$ approximately 65 to 80 per cent, $C_{10}$ approximately 10 to 30 per cent and $C_2$ at most 3 per cent, and has an acid number of at most 0.1, a saponification number of approximately 320 to 340 and an iodine number of at most 1.

Other suitable products of this class are Capmul MCT[1], Captex 300[1], Captex 800[1], Neobee M5[2], Mazol 1400[3] and Imwitor[4]

[1]=Capital City Products, P.O. Box 569, Columbus, Ohio, USA

[2]=Stepan, PVO Dept., 100 West Hunter Ave., Maywood, N.J. 07607, USA

[3]=Mazer Chemicals, 3938 Porett Drive, Gurnee, Ill., USA

[4]=Hüls AG, 14370 Marl, Germany

Other cosolvents are benzyl alcohol, which can simultaneously be used as a preservative, alcohols such as ethanol, glycol, glycerol, cyclic carbonates such as propylene carbonate. The cosolvents lie in concentrations of 30–85% by weight.

Further additives are stabilizers such as butylhydroxyanisole (BHA), butyl-hydroxy-toluene (BHT) or propyl gallate of up to 1000 ppm in total. Particularly suitable stabilizer combinations and concentrations are, for example, 100 ppm of BHA or 100 ppm of BHA plus 150 ppm of propyl gallate or 200 ppm of BHA plus 100 ppm of propyl gallate.

The viscosity of the formulations according to the invention is between 25 to 60 mPa.s (20° C.), preferably between 30 to 55 mPa.s (20° C.), particularly preferably between 35 and 51 mPa.s (20° C.).

The following examples illustrate the invention.

Note:

$$v/v = \frac{\text{volume}}{\text{volume}} \text{corresponds to per cent by volume}$$

$$m/v = \frac{\text{mass}}{\text{volume}}$$

1% m/v means, for example, 10 mg of active compound in 1 ml of solution.

EXAMPLE 1

| a) | | | b) | | |
|---|---|---|---|---|---|
| | Miglyol ® 812 | q.s. 100% v/v | | Miglyol ® 812 | q.s. 100% v/v |
| | Castor oil | 20% v/v | | Caster oil | 20% v/v |
| | Benzyl alcohol | 2% v/v | | Benzyl alcohol | 2% v/v |
| | Ivermectin | 1% m/v | | Ivermectin | 2% m/v |
| | Density | 0.954 g/ml | | Density | 0.956 g/ml |
| | Viscosity | 48 mPa.s at 20° C. | | Viscosity | 48 mPa.s at 20° C. |
| | | 95 mPa.s at 5° C. | | | 105 mPa.s at 5° C. |

EXAMPLE 2

| a) | | | b) | | |
|---|---|---|---|---|---|
| | Miglyol ® 812 | q.s. 100% v/v | | Miglyol ® 812 | q.s. 100% v/v |
| | Castor oil | 20% v/v | | Castor oil | 20% v/v |
| | Propylene carbonate | 3% v/v | | Propylene carbonate | 3% v/v |
| | Benzyl alcohol | 2% v/v | | Benzyl alcohol | 2% v/v |
| | Ivermectin | 1% m/v | | Ivermectin | 2% m/v |
| | Density | 0.962 g/ml | | Density | 0.964 g/ml |
| | Viscosity | 42 mPa.s at 20° C. | | Viscosity | 44 mPa.s at 20° C. |
| | | 91 mPa.s at 5° C. | | | 97 mPa.s at 5° C. |

EXAMPLE 3

| a) | Miglyol ® 812 | q.s. 100% v/v | b) | Miglyol ® 812 | q.s. 100% v/v |
|---|---|---|---|---|---|
| | Castor oil | 20% v/v | | Caster oil | 20% v/v |
| | Ivermectin | 1% m/v | | Ivermectin | 2% m/v |
| | Density | 0.952 g/ml | | Density | 0.954 g/ml |
| | Viscosity | 51 mPa.s at 20° C. | | Viscosity | 51 mPa.s at 20° C. |
| | | 105 mPa.s at 5° C. | | | 117 mPa.s at 5° C. |

EXAMPLE 4

| a) | Miglyol ® 812 | q.s. 100% v/v | b) | Miglyol ® 812 | q.s. 100% v/v |
|---|---|---|---|---|---|
| | Castor oil | 35% v/v | | Caster oil | 35% v/v |
| | Ivermectin | 1% m/v | | Ivermectin | 2% m/v |
| | Density | 0.939 g/ml | | Density | 0.941 g/ml |
| | Viscosity | 38 mPa.s at 20° C. | | Viscosity | 42 mPa.s at 20° C. |
| | | 75 mPa.s at 5° C. | | | 76 mPa.s at 5° C. |

EXAMPLE 5

| a) | Ethyl oleate | q.s. 100% v/v | b) | Ethyl oleate | q.s. 100% v/v |
|---|---|---|---|---|---|
| | Castor Oil | 45% v/v | | Castor Oil | 45% v/v |
| | Ivermectin | 1% m/v | | Ivermectin | 2% m/V |
| | Density | 0.916 g/ml | | Density | 0.918 g/ml |
| | Viscosity | 40 mPa.s at 20° C. | | Viscosity | 49 mPa.s at 20° C. |
| | | 91 mPa.s at 5° C. | | | 98 mPa.s at 5° C. |

EXAMPLE 6

| a) | Miglyol ® 840 | q.s. 100% v/v | b) | Miglyol ® 840 | q.s. 100% v/v |
|---|---|---|---|---|---|
| | Castor oil | 35% v/v | | Castor oil | 35% v/v |
| | Propylene glycol | 5% v/v | | Propylene glycol | 5% v/v |
| | Benzyl alcohol | 5% v/v | | Benzyl alcohol | 5% v/v |
| | Ivermectin | 1% m/v | | Ivermectin | 2% m/v |
| | Density | 0.952 g/ml | | Density | 0.954 g/ml |
| | Viscosity | 36 mPa.s at 20° C. | | Viscosity | 38 mPa.s at 20° C. |
| | | 76 mPa.s at 5° C. | | | 81 mPa.s at 5° C. |

EXAMPLE 7

| a) | Ethyl oleate | q.s. 100% v/v |
|---|---|---|
| | Castor oil | 40% v/v |
| | Propylene glycol | 5% v/v |
| | Benzyl alcohol | 5% v/v |
| | Ivermectin | 1% m/v |
| | Density | 0.926 g/ml |
| | Viscosity | 34 mPa.s at 20° C. |
| | | 70 mPa.s at 5° C. |

EXAMPLE 8

| a) | Miglyol ® 840 | q.s. 100% v/v |
|---|---|---|
| | Castor oil | 35% v/v |
| | Benzyl alcohol | 20% v/v |
| | Ivermectin | 1% m/v |
| | Density | 0.965 g/ml |
| | Viscosity | 28 mPa.s at 20° C. |
| | | 56 mPa.s at 5° C. |

EXAMPLE 9

| a) | Miglyol ® 840 | q.s. 100% v/v |
|---|---|---|
| | Castor Oil | 35% v/v |
| | Propylene carbonate | 10% v/v |
| | Benzyl alcohol | 5% v/v |
| | Ivermectin | 1% m/v |
| | Density | 0.975 g/ml |
| | Viscosity | 27 mPa.s at 20° C. |
| | | 53 mPa.s at 5° C. |

EXAMPLE 10

| | | |
|---|---|---|
| a) | Imwitor ® 408 | q.s. 100% v/v |
| | Castor oil | 30% v/v |
| | Ivermectin | 1% m/v |
| | Density | 0.953 g/ml |
| | Viscosity | 30 mPa.s at 20° C. |
| | | 66 mPa.s at 5° C. |

Imwitor® is a trade name of Hüls AG. Imwitor® 408 is 1,2-propanediol mono-dicaprylate (INCI (CTFA) name). According to provisional product information, Imwitor® 408 contains about 10% free propylene glycol and about 50% monoglycerides. It has a high dissolving power for Ivermectin (>20% m/v).

General Preparation Procedure for Examples 1 to 10 as Sterile Solutions for Injection:

The formulation auxiliaries are weighed into a stainless steel container and homogenized with stirring. The Ivermectin is introduced with further stirring. The mixture is warmed to 40 to 50° C. in order to accelerate the dissolution of the active compound (if possible with nitrogen aeration). After complete dissolution, the mixture is then sterile-filtered at the same temperature through a 0.22 µm filter (as a rule a 0.45 µm or 1 µm filter is preinserted). Aseptic dispensing into brown glass bottles follows.

The formulations prepared in this way are outstandingly tolerable when used in cattle. They are additionally stable on storage at temperatures between 4° C. and 60° C. over at least 6 weeks.

We claim:

1. Injection formulations of avermectins or milbemycins comprising a castor oil vehicle, characterized in that they have the following composition:
   1. avermectins or milbemycins 0.1 to 10% by weight;
   2. castor oil vehicle 15 to 50% by weight;
   3. one or more co-solvents from the series consisting of vegetable or synthetic fatty acid esters of mono- or polyhydric alcohols, aliphatic or aromatic alcohols, cyclic carbonates in concentrations of 30 to 85% by weight;
   4. optionally, further auxiliaries.

2. Formulations according to claim 1 of the following composition:
   0.1 to 10% m/v of an avermectin or milbemycin in a solvent mixture consisting of 15 to 50% v/v of castor oil, and 30 to 85% v/v of medium-chain triglyceride and/or propylene glycol octanoate/decanoate and/or ethyl oleate and 0 to 30% v/v of one or of a mixture of the solvents benzyl alcohol, propylene glycol or propylene carbonate, and optionally up to 1000 ppm of stabilizers.

3. Formulations according to claim 1 of the following composition:
   20 to 45% v/v of castor oil, 45 to 80% v/v of medium-chain triglycerides or propylene glycol octanoate/decanoate or ethyl oleate and 0 to 20% v/v of benzyl alcohol, 0 to 10% v/v of propylene glycol or propylene carbonate, and optionally up to 500 ppm of stabilizers.

4. Process for the preparation of the formulations according to claim 1, characterized by the step of mixing the ivermectins or milbemycins with castor oil, followed by adding the cosolvents or the step of dissolving the avermectins or milbemycins in a mixture of castor oil and the cosolvents.

5. A process for administering to animals the formulations of claim 1 comprising g injecting the animals with the formulations.

* * * * *